United States Patent
Zardi et al.

(10) Patent No.: US 7,982,068 B2
(45) Date of Patent: Jul. 19, 2011

(54) PROCESS FOR UREA PRODUCTION AND RELATED PLANT

(75) Inventors: Federico Zardi, Breganzona (CH); Paolo Brunengo, Lugano (CH); Paolo Sticchi, Massagno (CH)

(73) Assignee: Urea Casale S.A. (CH)

( * ) Notice: Subject to any disclaimer, the term of this patent is extended or adjusted under 35 U.S.C. 154(b) by 213 days.

(21) Appl. No.: 12/513,487

(22) PCT Filed: Oct. 9, 2007

(86) PCT No.: PCT/EP2007/008730
§ 371 (c)(1),
(2), (4) Date: Jul. 21, 2009

(87) PCT Pub. No.: WO2008/052639
PCT Pub. Date: May 8, 2008

(65) Prior Publication Data
US 2010/0063321 A1   Mar. 11, 2010

(30) Foreign Application Priority Data

Nov. 4, 2006 (EP) ..................................... 06022991

(51) Int. Cl.
*C07C 273/16* (2006.01)
*C07C 273/04* (2006.01)
(52) U.S. Cl. ................. 564/67; 564/70; 564/71; 564/72
(58) Field of Classification Search .................... 564/67, 564/70, 71, 72
See application file for complete search history.

(56) References Cited

U.S. PATENT DOCUMENTS

| 3,120,563 | A | 2/1964 | Bongard |
| 4,801,745 | A | 1/1989 | Meessen et al. |
| 4,864,059 | A | 9/1989 | Fujii |
| 5,597,454 | A | 1/1997 | Lee |
| 2002/0082451 | A1 | 6/2002 | Yoshida et al. |
| 2002/0151749 | A1 | 10/2002 | Pagani et al. |
| 2004/0116743 | A1 | 6/2004 | Mennen |

FOREIGN PATENT DOCUMENTS

| EP | 1719755 A1 | 11/2006 |
| NL | 8900152 A | 8/1990 |

*Primary Examiner* — Peter O Sullivan
(74) *Attorney, Agent, or Firm* — Akerman Senterfitt

(57) ABSTRACT

A process for urea production from ammonia and carbon dioxide, in which part of the aqueous solution comprising urea, ammonium carbamate and ammonia obtained in a urea synthesis section is subjected to dissociation in a treatment section operating at a predetermined medium pressure for the recovery of the ammonium carbamate and of the ammonia contained in it, comprises the steps of subjecting the urea aqueous solution resulting from the aforementioned dissociation step to decomposition in a low pressure urea recovery section and of using at least a part of the condensed steam, obtained by indirect thermal exchange with a second part of said aqueous solution comprising urea, ammonium carbmate and ammonia in a high-pressure stripping unit, as a heating fluid for the dissociation of the first part of the aqueous solution comprising urea, ammonium carbmate and ammonia in the medium-pressure treatment section.

21 Claims, 2 Drawing Sheets

PROCESS FOR UREA PRODUCTION AND RELATED PLANT

FIELD OF APPLICATION

In its most general aspect, the present invention concerns a process for urea production from ammonia and carbon dioxide, made to react at a predetermined high pressure in an appropriate synthesis section.

In particular, the invention refers to a process of the aforementioned type in which the product of the ammonia/carbon dioxide reaction, essentially consisting of an aqueous solution comprising urea, ammonium carbamate and ammonia, is subjected to a high-pressure recovery step of the ammonium carbamate and of the ammonia, which are recycled to the synthesis section, whereas the urea aqueous solution is sent to a urea recovery section operating at a predetermined low pressure to obtain urea with the least possible amount of possible residues of ammonia and carbon dioxide.

More specifically, the present invention concerns a process of the type considered, in which the aforementioned recovery of carbamate and ammonia comprises the steps of decomposition of the carbamate and stripping, preferably with a gaseous reactant (in particular $CO_2$), of the ammonia and carbon dioxide thus produced, in a respective stripping zone, subsequent recondensation, in a respective condensation zone, of said ammonia and carbon dioxide into carbamate that is recycled to the synthesis section and in which said steps, together with the urea synthesis reaction, are all carried out substantially at the same high pressure (for example 135-175 bar), constituting a loop called, in the technical field, "High Pressure Loop" or "High Pressure Synthesis Loop" (H.P. Loop).

The invention also refers to a plant for carrying out the aforementioned process.

PRIOR ART

It is well known to produce urea in industrial plants that carry out processes of the type specified above.

There is also a well known requirement to increase the capacity of such plants with respect to the design capacity for which such plants had originally been designed to face up to the ever greater requirement for synthesis urea.

For such a purpose, processes have been proposed in the field that foresee a medium pressure treatment step (10-40 bar) of a part of the aqueous solution comprising urea coming from the synthesis section for the recovery of the ammonium carbamate and ammonia contained in it.

In particular, such a medium pressure treatment section comprises a dissociation step followed by a stripping step with $CO_2$ feed of the aqueous solution comprising urea, ammonium carbamate and ammonia and a subsequent condensation step of the vapours (ammonia, $CO_2$ and water) thus obtained with the addition of feed ammonia and a carbamate aqueous solution (carbonate) coming from the low pressure urea recovery section. The carbamate aqueous solution obtained from the medium pressure condensation step is then recycled to the high pressure synthesis loop (H.P. loop).

A process of this type is for example described in WO-A-02 909 323 or else in NL-A-8 900 152.

Whilst they allow the aforementioned requirement to be at least partially satisfied, such processes for urea production of the aforementioned type have recognized drawbacks linked to the need to require the use of additional amounts of condensing water for the condensation of the feed $CO_2$ used as stripping agent in the medium pressure stripping step and of feed ammonia added at the medium pressure condensation step.

This additional use of condensation water is to the detriment of the conversion yield in the urea synthesis section and consequently of the efficiency and of the energy consumption of such a section as well as the efficiency and the energy consumption of the low pressure urea recovery section.

SUMMARY OF THE INVENTION

The technical problem underlying the present invention is that of devising and providing a process for urea production of the type considered above, in which a high production capacity of the plant intended to carry it out can be achieved and at the same time that ensures a high conversion yield of the carbon dioxide to urea in an efficient manner and with low energy consumption, overcoming the aforementioned drawbacks with reference to the prior art.

This problem is solved, according to the present invention, by a process for urea production from ammonia and carbon dioxide, comprising the steps of:

feeding ammonia and carbon dioxide into a urea synthesis section operating at a predetermined high pressure;

reacting said ammonia and said carbon dioxide in said synthesis section, obtaining an aqueous solution comprising urea, ammonium carbamate and ammonia;

feeding a part of said aqueous solution comprising urea, ammonium carbamate and ammonia to a treatment section operating at a predetermined medium pressure for the recovery of the ammonium carbamate and of the ammonia contained in it;

subjecting said part of aqueous solution comprising urea, ammonium carbamate and ammonia to dissociation in a dissociation unit of said treatment section, obtaining an urea aqueous solution and a vapour phase comprising ammonia, carbon dioxide and water;

subjecting said vapour phase comprising ammonia, carbon dioxide and water to condensation in said treatment section, obtaining an ammonium carbamate aqueous solution;

recycling said ammonium carbamate aqueous solution to said urea synthesis section;

characterized in that it comprises the further steps of:

feeding said urea aqueous solution obtained by dissociation in said treatment section to a decomposer of a urea recovery section operating at a predetermined low pressure;

subjecting said urea aqueous solution to decomposition in said decomposer of said urea recovery section, obtaining a concentrated urea solution and a second vapour phase comprising ammonia, carbon dioxide and water;

subjecting said second vapour phase to condensation in a condenser of said urea recovery section in fluid communication with said decomposer, obtaining a recycle ammonium carbamate aqueous solution, subjecting a second part of said aqueous solution comprising urea, ammonium carbamate and ammonia to stripping including heat in a stripping unit operating substantially at said predetermined high pressure, obtaining a second urea aqueous solution and a third vapour phase comprising ammonia, carbon dioxide and water, said heat being provided through indirect thermal exchange with a steam flow which condensates to condensed steam, using at least a part of said condensed steam as a heating fluid for dissociating said first part of the aqueous solution comprising urea, ammonium carbamate and ammonia in said dissociation unit of said medium pressure treatment section.

Preferably, the steam used for providing heat (thermal injection) and the condensed steam have a temperature between 200° C. and 235° C. and a pressure between 15 bar and 20 bar.

Preferably, at least a part of the condensed steam used in the medium pressure dissociation consists of 80% to 100% of the totality of the condensed steam obtained in the high pressure stripping unit by indirect thermal exchange.

Preferably, the stripping including heat of said aqueous solution comprising urea, ammonium carbamate and ammonia in said high pressure stripping unit is carried out also in the presence of carbon dioxide feed as a stripping agent.

Preferably, the process according to the present invention also comprises the steps of:

subjecting said third vapour phase comprising ammonia, carbon dioxide and water obtained in said stripping unit to condensation in a condensation unit operating substantially at said predetermined high pressure, obtaining a second aqueous solution of recycle ammonium carbamate, feeding said second urea aqueous solution obtained in said stripping unit in said decomposer of the urea recovery section operating at low pressure.

According to an embodiment of the process of the invention, the high-pressure condensation unit comprises a condenser of the submerged type and said condensation is carried out in said condenser by contacting said third vapour phase with a recycle ammonium carbamate aqueous solution and optionally liquid ammonia, and recovering the condensation heat through indirect thermal exchange with steam formation.

The term "submerged condenser" indicates a type of condenser comprising a tube bundle exchanger, per se conventional, in which the gaseous phase to be condensed as well as optionally the ammonium carbamate solution are made to flow in the tubes side while a means of indirect thermal exchange, such as water, is made to flow on the shell side. The heat released from the solution resulting from condensation is removed with the aid of the means flowing on the shell side which, due to the thermal exchange, is converted into steam.

According to an aspect of the present invention, the steam formed in said condenser of the high-pressure condensation unit is used in parallel with at least a part of said condensed steam as heating fluid for the dissociation of said first part of aqueous solution comprising urea, ammonium carbamate and ammonia in said dissociation unit of said medium-pressure treatment section.

Preferably, said steam formed in the condenser of the high-pressure condensation unit has a temperature from 135° C. to 165° C. and a pressure from 3 bar to 7 bar.

Preferably, the process according to the present invention also comprises the steps of:

feeding carbon dioxide to said condenser of said urea recovery section;

subjecting said carbon dioxide with said second vapour phase to condensation in said condenser of said urea recovery section obtaining a recycle ammonium carbamate aqueous solution.

In this respect, particularly advantageous results have been achieved by feeding an amount of carbon dioxide comprised between 1 and 10 wt. % of all of the feed carbon dioxide to said condenser of said urea recovery section.

Preferably, said first part of aqueous solution comprising urea, ammonium carbamate and ammonia fed to said treatment section operating at medium pressure is comprised between 10 and 50 wt. % of said aqueous solution comprising urea, ammonium carbamate and ammonia obtained in said synthesis section.

Again preferably, said medium pressure of the treatment section is comprised between 10 and 70 bar.

According to a preferred embodiment of the present invention, said recycle ammonium carbamate aqueous solution obtained in said condenser of the low pressure urea recovery section is fed to said condensation step of the vapour phase comprising ammonia, carbon dioxide and water in said medium-pressure treatment section.

Preferably, said condensation step of the vapour phase comprising ammonia, carbon dioxide and water in said medium-pressure treatment section is of the double-effect type.

Thanks to the process according to the present invention, a high production capacity is achieved as well as a high production yield while, at the same time, energy consumption is significantly reduced.

With regard to the energy consumption, a significant benefit derives from the use of at least part of the condensed steam, obtained by indirect thermal exchange in the high-pressure stripping unit, for the dissociation of the part of the aqueous solution comprising urea, ammonium carbamate and ammonia fed to the dissociation unit of the medium-pressure treatment section.

In this connection, it should be noted that the condensed steam coming out form the high-pressure stripping unit has relatively high temperature and pressure (high thermal level) which allow it to be efficiently used as a heating fluid for the aqueous solution comprising urea, carbamate and ammonia subjected to dissociation in the medium-pressure section.

In this way, most of the thermal content of condensed steam can be recovered, resulting in a significant reduction of the energy consumption required for urea synthesis.

Furthermore, according to an alternative embodiment of the invention, the steam at high temperature and pressure (high thermal level) formed in said condenser is advantageously used in parallel with a part of the condensed steam obtained in the high-pressure stripping unit for the dissociation in the medium-pressure section. In this way, the high thermal content of the remaining part of the condensed steam may be efficiently used for other purposes, in particular within the urea plant, thereby obtaining advantageously a substantial energy recover and a further reduction of energy consumption.

Thanks to the process according to the present invention, it has surprisingly and advantageously been found that the amount of condensation water (in absolute value) necessary to recycle the unreacted ammonia and the carbon dioxide in the form of ammonium carbamate to the synthesis section is substantially lower than the amount of condensation water (in absolute value) required to carry out such recycling with the processes according to the prior art, in which feed carbon dioxide and feed ammonia are fed to the medium pressure treatment section.

This is due to the fact that, with the same production capacity of the plant for urea production, the amount of ammonia and carbon dioxide to be recycled to the synthesis section in the form of ammonium carbamate is substantially lower with the process according to the present invention than with the processes of the prior art.

It follows that there is a significant increase in the conversion yield of the urea synthesis section, as well as of the overall yield of the H.P. Loop, to the great advantage of the efficiency and the energy consumption of the plant intended to carry out the process according to the present invention.

In accordance with a further aspect of the present invention, the present technical problem is solved by a plant for carrying out the aforementioned process, comprising a high-pressure urea synthesis section, a medium pressure treatment section of a first part of the urea solution produced in said synthesis section, comprising a dissociator and a condenser, a high-pressure stripping unit for a second part of the solution produced in said synthesis section, and a low pressure urea recovery section comprising a decomposer and a condenser, such sections being in fluid communication with each other, the plant being characterized in that it comprises a connection duct between said dissociator of the medium pressure treatment section and said decomposer of the low pressure urea recovery section and in that it comprises a connection duct between said high-pressure stripping unit and said dissociator of the medium-pressure treatment section for feeding condensed steam coming out from said stripping unit to said dissociator.

In accordance with the present invention, the plant for urea production according to the aforementioned process can be a brand new plant or else can be obtained by modifying a pre-existing plant in order to increase its capacity.

In this last case, in accordance with a further aspect of the present invention, a method for revamping a pre-existing plant for urea production from ammonia and carbon dioxide of the type comprising a high-pressure urea synthesis section, a high-pressure stripping unit for urea solution produced in said synthesis section and a low pressure urea recovery section comprising a decomposer and a condenser, such sections being in fluid communication with each other, is provided which is characterized in that it comprises the steps of:
- providing a medium pressure treatment section of a first part of the urea solution produced in said synthesis section, comprising a dissociator and a condenser, said medium pressure treatment section being placed in fluid communication with said high-pressure urea synthesis section and said low-pressure urea recovery section, respectively,
- providing a connection duct between said dissociator of the medium pressure treatment section and said decomposer of the low pressure urea recovery section, and
- providing a connection duct between said high-pressure stripping unit and said dissociator of the medium-pressure treatment section for feeding condensed steam coming out from said stripping unit to said dissociator.

Further features and advantages of the process for urea production according to the present invention shall become clearer from the following description of a preferred embodiment thereof, given for indicating and not limiting purposes with reference to the attached drawings.

DETAILED DESCRIPTION OF PREFERRED EMBODIMENTS

Figure 1:
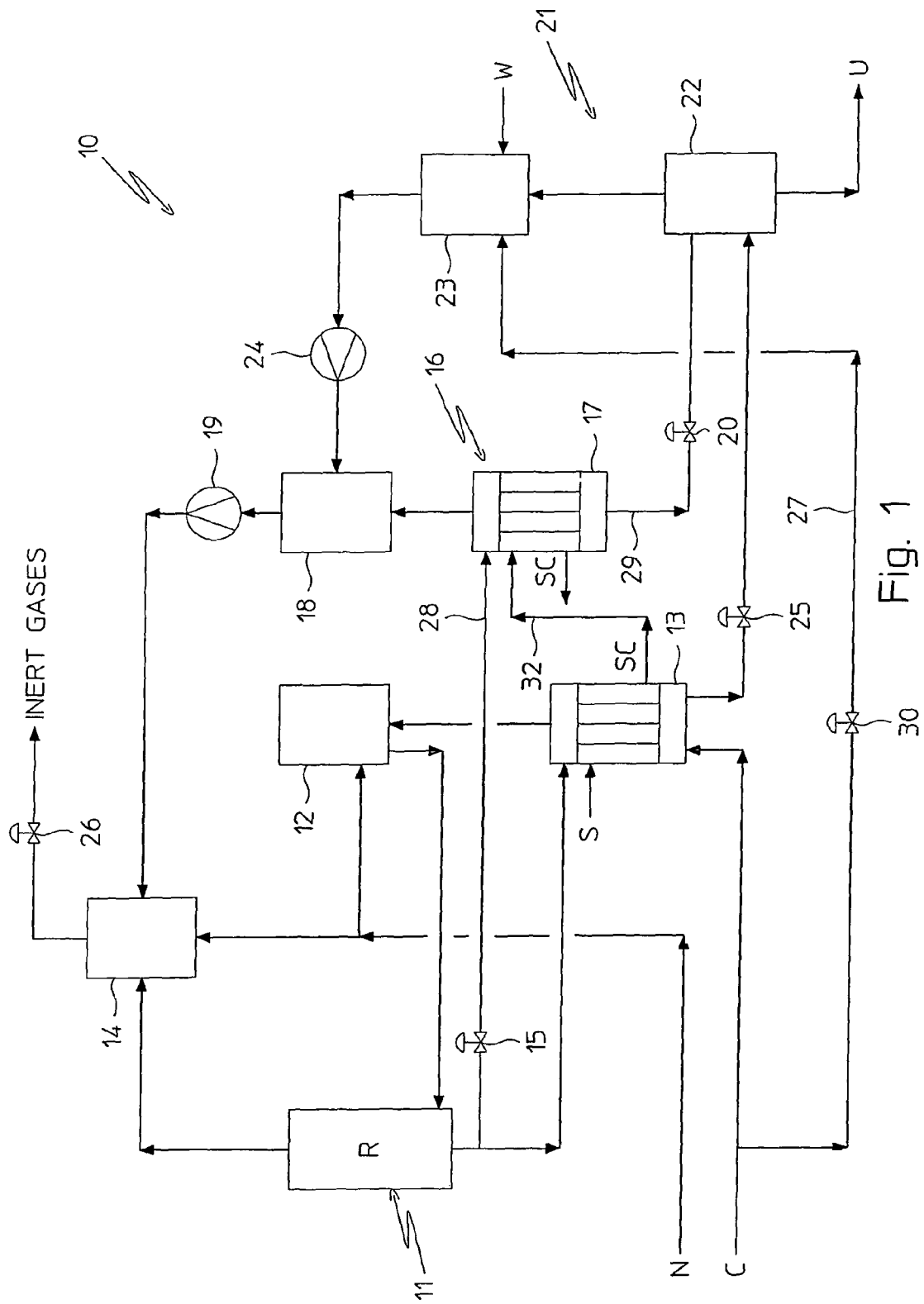
FIG. 1 schematically shows a plant for urea production that carries out the process according to an embodiment of the present invention.

With reference to FIG. 1, a plant, wholly indicated with 10, for urea production is shown, which carries out the process according to an embodiment of the present invention.

According to the aforementioned process for urea production, ammonia N and carbon dioxide C are fed into an appropriate synthesis section 11. In the example of FIG. 1, the urea synthesis section comprises a single reactor R.

In particular, according to such an example, the ammonia N is fed to the reactor R through a condenser 12 and the carbon dioxide C is in turn fed to the reactor R through a stripper 13 and the condenser 12.

The synthesis section 11 (reactor R), the condensation unit (condenser 12), the stripping unit (stripper 13), together with a scrubber 14 (that shall be described hereafter in greater detail), all operate substantially at the same high pressure, thus constituting the high pressure synthesis loop (H.P. Loop) of the process of the present invention.

In the reactor R, or rather in the synthesis section 11, the ammonia and carbon dioxide are made to react at the aforementioned predetermined high pressure (for example comprised between 130 and 170 bar) and at a predetermined high temperature (for example comprised between 160 and 200° C.). From the reactor R an aqueous solution comprising urea, ammonium carbamate and ammonia is obtained.

A part of the aqueous solution comprising urea, ammonium carbamate and ammonia exiting the reactor R is suitably decompressed in a per se conventional way for example by means of a valve 15 and fed to a treatment section 16 of such an aqueous solution operating at a predetermined medium pressure, for example comprised between 10 and 70 bar, preferably comprised between 15 and 25 bar, and even more preferably comprised between 18-20 bar.

For the recovery of the ammonium carbamate and the ammonia, the part of aqueous solution comprising urea, ammonium carbamate and ammonia suitably decompressed is fed to a medium pressure dissociator 17 at the treatment section 16 and subjected to dissociation obtaining an urea aqueous solution and a vapour phase comprising ammonia, carbon dioxide and water. In particular, such a part of aqueous solution comprising urea, ammonium carbamate and ammonia is subjected in the dissociator 17 to thermal dissociation.

The vapour phase comprising ammonia, carbon dioxide and water thus obtained is then fed and subjected to condensation in a medium pressure condenser 18 of the treatment section 16. In the condenser 18 an ammonium carbamate aqueous solution is obtained that exits the condenser 18 and is recycled to the urea synthesis section 11 (reactor R).

In the example of FIG. 1, the carbamate aqueous solution exiting the medium pressure condenser 18 is suitably compressed in a per se conventional way for example by means of a pump 19 and recycled to the reactor R of the high pressure urea synthesis section 11 through the scrubber 14 and the high pressure condenser 12.

According to an alternative embodiment of the present invention, not represented, at least a part of the carbamate aqueous solution exiting the medium pressure condenser 18 is fed, suitably compressed, directly to the high pressure condenser 12 to then flow into the reactor R.

The remaining part of the aqueous solution comprising urea, ammonium carbamate and ammonia, coming out from the reactor R and not sent to the medium-pressure treatment section 16, is subjected to the step of recovering ammonium carbamate and ammonia contained in such a solution, in the high-pressure synthesis loop of this process.

In particular, according to the example of FIG. 1, the remaining part of the aqueous solution comprising urea, ammonium carbamate and ammonia coming out from the reactor R of the synthesis section 11 is fed to the stripper 13 of the high-pressure stripping unit where it is subjected to decomposition and stripping with $CO_2$ e heat. The heat is provided by indirect thermal exchange with a steam flow S having high temperature and pressure (for example 211-223° C. and 20-25 bar). The $CO_2$ as stripping agent is instead provided using feed carbon dioxide C.

In accordance with the present invention, the process for urea production advantageously foresees that at least a part of the condensed steam SC coming out from the stripper 13 is fed, through a duct 32, to the dissociator 17. In the dissociator 17, the condensed steam SC, which ahs relatively high temperature and pressure (high thermal level for example 211-223° C. and 20-25 bar) is advantageously used to provide the heat necessary to dissociate the part of the aqueous solution comprising urea, ammonium carbamate and ammonia coming out from the reactor R and fed to said dissociator 17.

The process according to the invention further comprises the further step of feeding the urea aqueous solution obtained by dissociation in the medium pressure dissociator 17 of the treatment section 16 to a decomposer of a urea recovery section 21 operating at a predetermined low pressure, for example comprised between 1.5 and 9.5 bar, preferably comprised between 3 and 5 bar.

For this purpose, the urea aqueous solution exiting the dissociator 17 is suitably decompressed in a per se conventional way for example by means of a valve 20.

In particular, as represented in the preferred embodiment of the process according to the present invention of FIG. 1, the urea aqueous solution exiting the dissociator 17 of the treatment section 16 is directly fed to the decomposer 22 of the urea recovery section 21.

Moreover, again in accordance with the example of FIG. 1, a part of the feed carbon dioxide C is preferably and advantageously fed to a condenser 23 of the low pressure urea recovery section 21.

For this purpose, such a part of feed carbon dioxide C sent to the condenser 23 is suitably decompressed in a per se conventional way for example by means of a valve 30.

In the decomposer 22 of the low pressure urea recovery section 21, the urea aqueous solution coming out from the dissociator 17 of the medium pressure treatment section 16 is subjected to decomposition obtaining a concentrated urea solution U and a second vapour phase comprising ammonia, carbon dioxide and water.

The concentrated urea solution U, for example with a urea concentration comprised between 60 and 80 wt. %, exits the decomposer 22 of the urea recovery section 21 to be subjected to the final urea treatment steps (per se conventional and therefore not represented) of the process for urea production, such as the vacuum decomposition step and the granulation or prilling step of the molten urea thus obtained.

The second vapour phase comprising ammonia, carbon dioxide and water obtained in the decomposer 22 of the urea recovery section 21 is, on the other hand, sent to the condenser 23 of the same section 21 and advantageously subjected to condensation obtaining a recycle carbamate aqueous solution.

Preferably, as represented in the example of FIG. 1, the second vapour phase comprising ammonia, carbon dioxide and water is subjected to condensation together with the feed carbon dioxide C fed to said condenser 23.

A suitable amount of a carbamate aqueous solution (carbonate) having a condensation water content comprised between 30 and 80 wt. % is also fed to the condenser 23 of the low pressure urea recovery section 21, to allow the second vapour phase and the feed carbon dioxide C, respectively, to condense to ammonium carbamate.

The carbamate aqueous solution W (carbonate) generally comes from a treatment section of the process condensate and/or from an ammonia liquor reservoir, per se conventional and not represented in FIG. 1.

Preferably, as represented in the example of FIG. 1, the recycle carbamate aqueous solution obtained in the condenser 23 of the low pressure urea recovery section 21 is, according to the present process, fed into the medium pressure condenser 18 of the treatment section 16 for the absorption (condensation) of the vapour phase comprising ammonia, carbon dioxide and water coming from the medium pressure dissociator 17.

In this case, the step of compressing the recycle carbamate aqueous solution exiting the condenser 23, to the operating pressure of the treatment section 16 is also foreseen in a per se conventional way for example by means of a pump 24.

According to an alternative embodiment of the process according to the present invention, not represented, the condensation step in the condenser 18 of the medium pressure treatment section 16 is of the double effect type, in which the condensation heat, instead of being dissipated in a cooling fluid (generally cooling water), is advantageously exploited to further concentrate the concentrated urea solution U exiting the decomposer 22 of the low pressure urea recovery section.

In this case, the condensation heat that develops during the condensation of the vapour phase is transmitted by indirect heat exchange to the concentrated urea solution U, allowing the decomposition and therefore the separation of a part of the ammonium carbamate, ammonia and water still present in such a solution and thus further concentrating the urea contained in it.

Turning to the stripper 13 of the high-pressure stripping unit, ammonia and carbon dioxide produced from the stripping of the remaining part of aqueous solution comprising urea, ammonium carbamate and ammonia exiting the reactor R, are re-condensed to ammonium carbamate in the condenser 12 of the high-pressure condensation unit and recycled, in the ammonium carbamate form, to the reactor R of the urea synthesis section 11.

The condensation in the high pressure condenser 12 of the ammonia and carbon dioxide coming from the stripper 13 is made to occur by absorption of such gases with the feed ammonia N (liquid) and with the carbamate aqueous solution coming, suitably compressed, from the condenser 18 of the medium pressure treatment section 16, through the scrubber 14.

The aqueous solution comprising urea, ammonium carbamate and ammonia obtained in the stripper 13 following the aforementioned decomposition and stripping steps with $CO_2$ is suitably decompressed in a per se conventional way for example by means of a valve 25 at the operating pressure of the urea recovery section 21 and fed to the low pressure decomposer 22 of such a section 21. Here, such a solution is subjected to decomposition, together with said urea aqueous solution coming from the dissociator 17 of the medium pressure treatment section 16, obtaining the concentrated urea solution U and the second vapour phase comprising ammonia, carbon dioxide and water, described above.

The unreacted carbon dioxide and ammonia and water in vapour phase present in the urea synthesis section 11, or rather in the reactor R, are made to exit the latter and fed to the high pressure scrubber 14. These vapours generally also comprise inert gases (for example air) present in the feed carbon dioxide C.

In the scrubber 14, the aforementioned vapours are subjected to a washing treatment with the carbamate aqueous solution coming, suitably compressed, from the condenser 18 of the medium pressure treatment section 16, for the recovery of the carbon dioxide and ammonia present in them and the separation of the inert gases. The inert gases thus separated are then released into the atmosphere in a per se conventional manner, moreover foreseeing suitable decompression thereof for example by means of a valve 26. Alternatively, such inert gases can be recycled in other parts of the plant (not represented). The carbon dioxide and ammonia absorbed in the carbamate aqueous solution coming from the condenser 18 are, on the other hand, recycled to the urea synthesis section 11, or rather to the reactor R, through the high pressure condenser 12.

Figure 2:
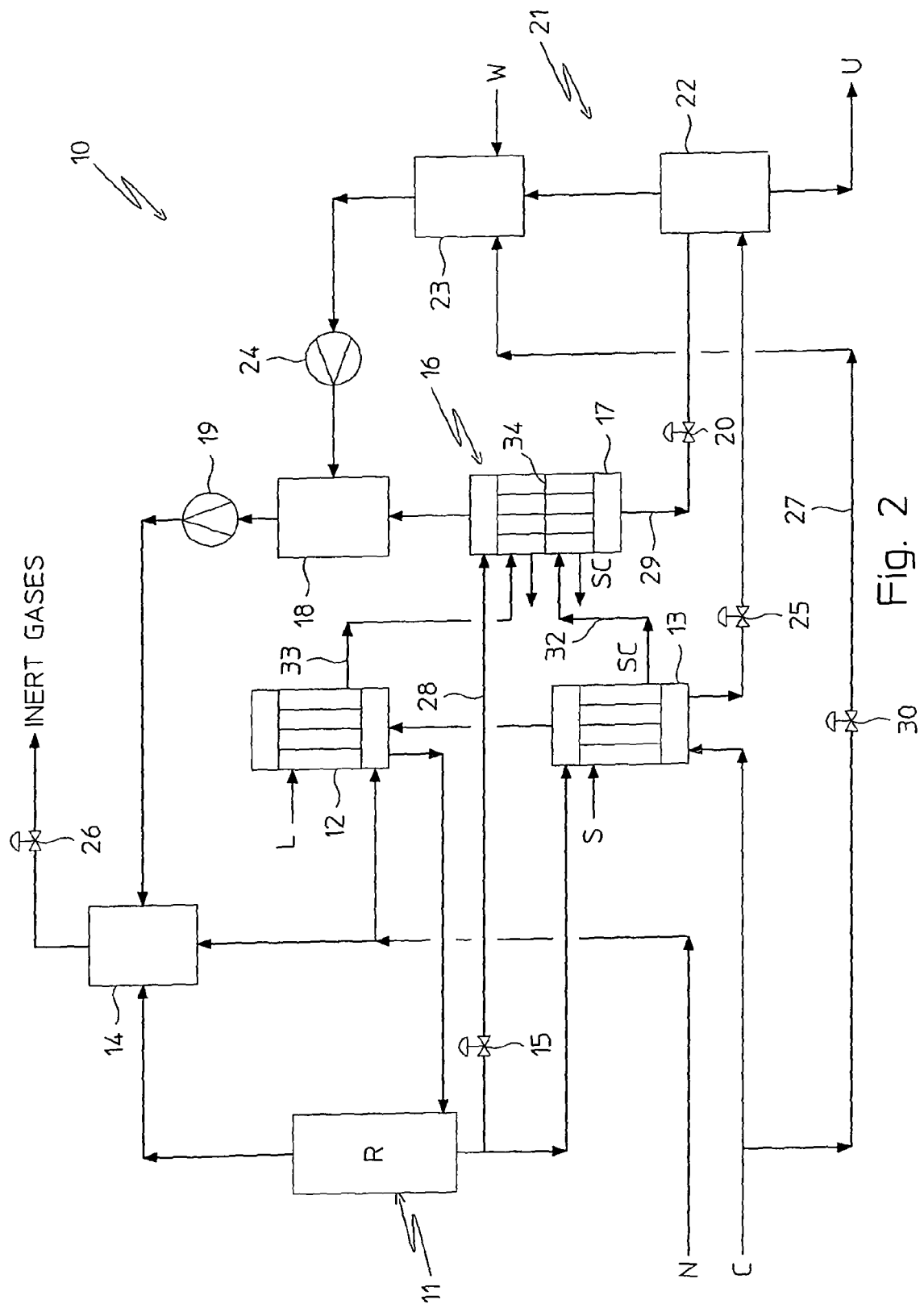
FIG. 2 schematically shows a plant for urea production that carries out the process according to another embodiment of the present invention.

With reference now to FIG. 2, a plant, wholly indicated with 110, for urea production is shown, which carries out the process according to another embodiment of the present invention.

This process for urea production differs from that described above in that the steam obtained from the condenser 12 of the high-pressure condensation unit is fed, through a duct 33 and in parallel with a part of the condensed steam SC coming from the high-pressure stripping unit (stripper 13), to the dissociator 17 of the medium-pressure treatment section 16.

In the dissociator 17, the condensed steam SC and the steam coming from the high-pressure condenser 12, which has a relatively high temperature and pressure (high thermal level) are advantageously used for providing the heat necessary to dissociate the part of aqueous solution comprising urea, ammonium carbamate and ammonia coming out from the reactor R and fed to said dissociator 17.

To this purpose, the condensed steam SC and the steam coming from the condenser 12 are made to flow, shell side, independently, within respective chambers of the dissociator 17, which are separated to each other in a per se conventional way, for example through an appropriate tube plate 34.

Advantageously, in accordance with this embodiment of the invention, the condenser 12 of the high-pressure section 11 is preferably of the submerged type with a tube bundle exchanger in which the cooling liquid L, usually water, flowing said exchanger shell side, is converted in steam due to the thermal exchange with the solution resulting from the combination of the ammonium carbamate solution coming from the condenser 18 of the medium-pressure treatment section 16 (via scrubber 14), of the feed ammonia N and of the vapour phase to be condensed coming from the high-pressure stripping unit (stripper 13).

With the process according to the present invention, particularly advantageous results have been obtained by feeding steam S at a temperature from 211° C. to 223° C. and a pressure from 20 bar to 25 bar to the stripper 13 and by feeding to the dissociator 17 100% of condensed steam SC coming from the stripper 13 and having substantially the same temperature and pressure, then a high thermal level. Advantageous results have been also obtained by feeding to the dissociator 17 in addition to the condensed steam SC and in parallel to the latter, also a part of the steam coming from the condenser 12 of the high-pressure condensation unit and/or by feeding an amount of feed carbon dioxide C comprised between 1 and 5 wt. %, even more preferably comprised between 2 and 3 wt. %, of all of the feed carbon dioxide C fed to the plant 10, to the condenser 23 of the low pressure urea recovery section 21.

Moreover, the part of aqueous solution comprising urea, ammonium carbamate and ammonia sent to the medium pressure treatment section 16 is preferably comprised between 10 and 50 wt. %, even more preferably comprised between 10 and 25 wt. %, of the aqueous solution coming from the urea synthesis section 11.

With reference to the figures, the structural features of the plant 10 for synthesis urea production from ammonia and carbon dioxide according to the process of the present invention just described shall now be better specified.

In accordance with the present invention, the plant 10 comprises a high pressure urea synthesis section 11, a high-pressure striping unit (stripper 13), a medium pressure treatment section 16 and a low pressure urea recovery section 21 arranged in fluid communication with each other.

The treatment section 16 advantageously comprises a medium pressure dissociator 17 and a medium pressure condenser 18 in fluid communication with each other. In turn, the urea recovery section 21 comprises a low pressure decomposer 22 and a low pressure condenser 23 in fluid communication with each other.

In the plant 10 respective feed ducts are foreseen of the reactants, carbon dioxide C and ammonia N, and of an carbamate aqueous solution W (carbonate) comprising condensation water, as well as connection ducts between the different sections and the corresponding apparatuses, schematically represented in FIGS. 1 and 2 by the different flow lines.

In particular, in the plant 10 connection ducts 28 and 29 are advantageously foreseen for the direct connection between the urea synthesis section 11 and the dissociator of the medium pressure treatment section 16, and between this apparatus and the decomposer 22 of the low pressure urea recovery section 21, respectively.

According to the present invention, a connection duct 32 is also foreseen in the plant 10 for feeding condensed steam SC coming from the stripper 13 of the stripping unit to the dissociator 17.

Moreover, according to the preferred embodiment of the present invention, a duct 27 for feeding feed carbon dioxide C to the condenser 23 of the low pressure urea recovery section 21 is also foreseen.

According to an alternative embodiment, not represented, of the plant 10 according to the present invention, the medium pressure condenser 18 comprises a conventional tube bundle, in fluid communication, on the inside, i.e. tube side, with the concentrated urea solution U exiting the low pressure decomposer 22, and in fluid communication, on the outside, i.e. shell side, with the vapour phase comprising ammonia, carbon dioxide and water coming from the medium pressure dissociator 17 as well as with the recycle carbamate aqueous solution coming from the low pressure condenser 23, to obtain the double effect described above.

According to the embodiment of the present invention shown in FIG. 2, the plant 10 further comprises a connection duct 33 between the condenser 12 of the high-pressure condensation unit and the dissociator 17 of the medium-pressure section 16.

In this connection, the condenser 12 of the high-pressure stripping unit is of the submerged type comprising a tube bundle and the connection duct 33 is in fluid communication shell side with said exchanger.

From the previous description it can clearly be seen that the process for urea production according to the invention solves the technical problem and achieves numerous advantages the first of which lies in the fact that it allows to obtain a significant reduction of the energy consumption due to the recover of at least part of the thermal content of the condensed steam coming from the high-pressure stripping unit for heating the part of solution comprising urea, ammonium carbamate and ammonia coming from the high-pressure synthesis section and subjected to dissociation in the medium-pressure treatment section.

Furthermore, with the process of the invention, a high overall conversion yield is obtained in the high pressure loop compared with what proposed by the prior art, and in particular in the urea synthesis section, for example comprised between 58 and 62 wt. %, also in the case of revamping pre-existing plants of large capacity for example plants producing between 3000 and 4500 Metric Ton/day of urea.

A further advantage is that, thanks to the present invention and in particular to the high conversion yield, it is possible to reduce the energy consumption of the high pressure synthesis loop as well as of the low pressure urea recovery section, with respect to the processes according to the prior art. It follows from this that with the same energy consumption and size of the apparatuses that constitute the plant for urea production, the process according to the present invention allows operation in such a plant with a higher production capacity with respect to what is allowed with the processes according to the prior art. In other words, with the same production capacity, the plant intended to carry out the process according to the present invention is smaller in size, and thus more cost-effective and with less operating costs, with respect to the plant necessary to obtain such a capacity with the methods of the prior art.

Moreover, the actuation of the process is particularly simple and reliable, and does not require large investment costs.

The aforementioned advantages are mainly linked to the fact that thanks to the studies carried out by the Applicant it has surprisingly been found that by subjecting the urea aqueous solution obtained by dissociation in the medium pressure treatment section to low pressure decomposition, the amount (in absolute value) of condensation water contained in the carbamate aqueous solution W (carbonate) required for such condensation to ammonium carbamate is substantially less than the amount of condensation water necessary with the methods according to the prior art.

Given that such condensation water is recycled to the urea synthesis section together with the ammonium carbamate and given that water is a reaction product in urea synthesis and that therefore has a negative influence upon the conversion of the reactants, the fact of managing to substantially reduce such an amount of condensation water has advantageously involved a corresponding increase in the conversion yield with respect to the processes according to the prior art.

In particular, unlike the present invention, the processes according to the prior art necessarily foresee, in the medium pressure treatment section, a stripping step with feed carbon dioxide of the urea aqueous solution previously obtained by thermal dissociation in such a section and a condensation step with the addition of feed ammonia. In order to be able to efficiently and totally condense such amounts of feed carbon dioxide and ammonia introduced into the medium pressure treatment section to ammonium carbamate, it is thus necessary to feed a substantially larger amount (in absolute value) of condensation water to the low pressure urea recovery section than that required with the process according to the present invention.

As an example, it has advantageously been noted that, with the same operating conditions, the aforementioned amount of condensation water contained in the carbamate aqueous solution W (carbonate) is 10-25 wt. % less with the process according to the present invention with respect to the prior art, with a corresponding increase in the conversion yield in the high pressure urea synthesis section of 2-3%.

Amongst the numerous advantages achieved by the present invention it is important to quote the possibility of increasing the production capacity of pre-existing plants for urea production from ammonia and carbon dioxide, with respect to the design capacity for which such plants had originally been designed, in a simple, effective and reliable way and at the same time reducing operating costs and energy consumption of the pre-existing plant. Advantageously, this is also possible for substantial increases in capacity, for example of 30-50%, with respect to the design capacity of the pre-existing plant.

In accordance with the preferred embodiment of the present invention represented in FIG. 1, the plant 10 for urea production is obtained from a revamping method (modernization) of a pre-existing plant for urea production from ammonia and carbon dioxide of the type comprising a high pressure urea synthesis section 11, a high-pressure stripping unit 13 for the urea solution produced in said synthesis section 11 and a low pressure urea recovery section 21 comprising a decomposer 22 and a condenser 23, such sections 11, 13 and 21 being arranged in fluid communication with each other, characterized in that it comprises the steps of:

providing a medium pressure treatment section 16 of a part of the urea solution produced in said synthesis section 11, comprising a dissociator 17 and a condenser 18, said medium pressure treatment section 16 being placed in fluid communication with said high pressure urea synthesis section and said low pressure urea recovery section 11, 21, respectively;

providing a connection duct 29 between said dissociator 17 of the medium pressure treatment section 16 and said decomposer 22 of the low pressure urea recovery section 21;

providing a connection duct 32 between said high-pressure stripping unit 13 and said dissociator 17 of the medium-pressure treatment section 16 for feeding condensed steam coming from said stripping unit 13 to said dissociator 17.

Preferably, the revamping method according to the invention is characterized in that it further comprises the step of:

providing a connection duct 33 between a high-pressure condensation section 12 of the pre-existing urea production plant and said dissociator 17 of the medium-pressure section 16 for feeding steam coming from said condensation unit 12 to said dissociator 17.

Still preferably, the method according to the present invention foresees the further step of providing a duct 27 for feeding feed carbon dioxide C to said condenser 23 of the low pressure urea recovery section 21.

Of course, a man skilled in the art can bring numerous modifications and variants to the process for urea production described above in order to satisfy contingent and specific requirements, all of which are in any case covered by the scope of protection of the present invention, as defined by the following claims.

The invention claimed is:

1. A process for urea production from ammonia and carbon dioxide, comprising the steps of:

feeding ammonia and carbon dioxide into a urea synthesis section operating at a predetermined high pressure;

reacting said ammonia and said carbon dioxide in said synthesis section obtaining an aqueous solution comprising urea, ammonium carbamate and ammonia;

feeding a first part of said aqueous solution comprising urea, ammonium carbamate and ammonia to a treatment section operating at a predetermined medium pressure for the recovery of the ammonium carbamate and of the ammonia contained in it;

subjecting said first part of aqueous solution comprising urea, ammonium carbamate and ammonia to dissociation in said treatment section obtaining an urea aqueous solution and a vapour phase comprising ammonia, carbon dioxide and water;

subjecting said vapour phase comprising ammonia, carbon dioxide and water to condensation in said treatment section obtaining an ammonium carbamate aqueous solution;

recycling said ammonium carbamate aqueous solution to said urea synthesis section;

feeding said urea aqueous solution obtained by dissociation in said treatment section to a decomposer of a urea recovery section operating at a predetermined low pressure;

subjecting said urea aqueous solution to decomposition in said decomposer of said urea recovery section obtaining a concentrated urea solution and a second vapour phase comprising ammonia, carbon dioxide and water;

subjecting said second vapour phase to condensation in a condenser of said urea recovery section in fluid communication with said decomposer obtaining a first recycle ammonium carbamate aqueous solution;

subjecting a second part of said aqueous solution comprising urea, ammonium carbamate and ammonia to stripping including heat in a stripping unit operating substantially at said predetermined high pressure, obtaining a second urea aqueous solution and a third vapour phase comprising ammonia, carbon dioxide and water, said heat being provided through indirect thermal exchange with a steam flow which condensates to condensed steam; and using at least a part of said condensed steam as a heating fluid for dissociating said first part of the aqueous solution comprising urea, ammonium carbamate and ammonia in said dissociation unit of said medium pressure treatment section.

2. The process according to claim 1, wherein said steam used for providing heat and said condensed steam has a temperature from 200° C. to 235° C. and a pressure from 15 bar to 30 bar.

3. The process according to claim 1, wherein said at least a part of the condensed steam used for the medium-pressure dissociation consists of 80% to 100% of the totality of the condensed steam obtained by indirect thermal exchange in the high-pressure stripping unit.

4. The process according to claim 1, wherein it comprises the further steps of:

subjecting said third vapour phase comprising ammonia, carbon dioxide and water obtained in said stripping unit to condensation in a condensation unit operating substantially at said predetermined high pressure, obtaining a second aqueous solution of recycle ammonium carbamate, feeding said second urea aqueous solution obtained in said stripping unit in said decomposer of the urea recovery section operating at low pressure.

5. The process according to claim 4, wherein said high-pressure condensation unit comprises a condenser of the submerged type and said condensation is carried out in said condenser by contacting said third vapour phase with a recycle ammonium carbamate aqueous solution and optionally liquid ammonia, and recovering the condensation heat through indirect thermal exchange with steam formation.

6. The process according to claim 5, wherein it further comprises the step of:

using the steam formed in said condenser of the high-pressure condensation unit in parallel with at least a part of said condensed steam as heating fluid for the dissociation of said first part of aqueous solution comprising urea, ammonium carbamate and ammonia in said dissociation unit of said medium-pressure treatment section.

7. The process according to claim 5, wherein said recycle ammonium carbamate solution comprises at least a part of the solution obtained from the condensation in said medium-pressure treatment section.

8. The process according to claim 7, wherein said at least a part of the solution obtained from the condensation in said medium-pressure treatment section is recycled to said condenser of the high-pressure condensation unit through a scrubber.

9. The process according to claim 1, wherein it comprises the further steps of:

feeding carbon dioxide to said condenser of said urea recovery section;

subjecting said carbon dioxide with said second vapour phase to condensation in said condenser of said urea recovery section obtaining a recycle ammonium carbamate aqueous solution.

10. The process according to claim 9, wherein an amount of carbon dioxide comprised between 1 and 10 wt. % of all of the feed carbon dioxide is fed to said condenser of said urea recovery section.

11. The process according to claim 1, wherein said part of aqueous solution comprising urea, ammonium carbamate and ammonia fed to said treatment section operating at medium pressure is comprised between 10 and 50 wt. % of said aqueous solution comprising urea, ammonium carbamate and ammonia obtained in said synthesis section.

12. The process according to claim 1, wherein said medium pressure of the treatment section is comprised between 10 and 70 bar.

13. The process according to claim 1, wherein said recycle ammonium carbamate aqueous solution obtained in said condenser of the low pressure urea recovery section is fed to said condensation step of the vapour phase comprising ammonia, carbon dioxide and water in said treatment section.

14. The process according to claim 1, wherein said condensation step of the vapour phase comprising ammonia, carbon dioxide and water in said treatment section is of the double effect type.

15. A plant for urea production from ammonia and carbon dioxide according to the process of claim 1, comprising:

a high-pressure urea synthesis section;

a medium pressure treatment section for a first part of the urea solution produced in said synthesis section, comprising a dissociator and a condenser;

a high-pressure stripping unit for a second part of the urea solution produced in said synthesis section;

a low pressure urea recovery section comprising a decomposer and a condenser, such sections being in fluid communication with each other;

a connection duct between said dissociator of the medium pressure treatment section and said decomposer of the low pressure urea recovery section; and a connection duct between said high-pressure stripping unit and said dissociator of the medium-pressure section for feeding condensed steam coming from said stripping unit to said dissociator.

16. The plant according to claim 15, further comprising a duct for feeding feed carbon dioxide to said condenser of the low pressure urea recovery section.

17. The plant according to claim 15, further comprising a connection duct between a high-pressure condensation unit and said dissociator of the medium-pressure section for feeding steam coming from said condensation unit to said dissociator.

18. The plant according to claim 15, wherein said condenser of the medium pressure treatment section comprises a tube bundle in fluid communication, tube side, with a concentrated urea solution exiting said decomposer of the low pressure urea recovery section, and shell side, with a vapour phase comprising ammonia, carbon dioxide and water exiting said dissociator of the medium pressure treatment section as well as with a recycle carbamate aqueous solution exiting said condenser of the low pressure urea recovery section.

19. A revamping method of a pre-existing plant for urea production from ammonia and carbon dioxide of the type comprising a high pressure urea synthesis section, a high-pressure stripping unit for the urea solution produced in said high-pressure synthesis section and a low pressure urea recovery section comprising a decomposer and a condenser, such sections being in fluid communication with each other, wherein it comprises the steps of:

providing a medium pressure treatment section of a part of the urea solution produced in said synthesis section, comprising a dissociator and a condenser, said medium pressure treatment section being placed in fluid communication with said high pressure urea synthesis section and said low pressure urea recovery section, respectively;

providing a connection duct between said dissociator of the medium pressure treatment section and said decomposer of the low pressure urea recovery section; and providing a connection duct between said high-pressure stripping unit and said dissociator of the medium-pressure section for feeding condensed steam coming from said stripping unit to said dissociator.

20. The method according to claim 19, wherein it comprises the further step of:

providing a duct for feeding feed carbon dioxide to said condenser of the low pressure urea recovery section.

21. The method according to claim 19, wherein it comprises the further step of:

providing a connection duct between a high-pressure condensation unit of the pre-existing urea production plant and said dissociator of the medium-pressure section for feeding steam coming from said condensation unit to said dissociator.

* * * * *